(12) United States Patent
Orszulak

(10) Patent No.: US 7,513,896 B2
(45) Date of Patent: Apr. 7, 2009

(54) DUAL SYNCHRO-RESONANT ELECTROSURGICAL APPARATUS WITH BI-DIRECTIONAL MAGNETIC COUPLING

(75) Inventor: James H. Orszulak, Nederland, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 613 days.

(21) Appl. No.: 11/338,309

(22) Filed: Jan. 24, 2006

(65) Prior Publication Data

US 2007/0173810 A1   Jul. 26, 2007

(51) Int. Cl.
*A61B 18/18* (2006.01)

(52) U.S. Cl. .............. 606/34; 606/32; 606/33; 606/37; 606/39; 606/40; 606/41; 606/42

(58) Field of Classification Search .......... 606/34, 606/37–42, 45–52; 342/175; 361/157, 160, 361/182–184; 455/41.1, 66.1, 90.1, 106; 333/101, 175

See application file for complete search history.

(56) References Cited

U.S. PATENT DOCUMENTS

| | | | |
|---|---|---|---|
| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |
| 2,827,056 | A | 3/1958 | Degelman |
| 2,849,611 | A | 8/1958 | Adams |
| 2,982,881 | A | 5/1961 | Reich |
| 3,058,470 | A | 10/1962 | Seeliger et al. |
| 3,089,496 | A | 5/1963 | Degelman |
| 3,163,165 | A | 12/1964 | Islikawa |
| 3,252,052 | A | 5/1966 | Nash |
| 3,391,351 | A | 7/1968 | Trent |

(Continued)

FOREIGN PATENT DOCUMENTS

DE   179607   3/1905

(Continued)

OTHER PUBLICATIONS

International Search Report EP 06000708.5 dated Apr. 21, 2006.

(Continued)

*Primary Examiner*—Sam Chuan C. Yao
*Assistant Examiner*—Samantha Muro

(57) ABSTRACT

An electrosurgical generator is disclosed, which includes an RF output stage connected to a DC power supply and first and second connections. The first connection includes a first switching component and a first parallel inductor-capacitor resonant circuit. The second connection includes a second switching components and a second parallel inductor-capacitor resonant circuit. The first and second switching components are configured to open and close at a predetermined frequency based on a phase-correlated dual drive signal emitted by a driver and are in a 180 degree out-of-phase relationship. The first parallel inductor-capacitor resonant circuit is further configured to produce a first half-sinusoidal waveform and the second parallel inductor-capacitor resonant circuit is configured to produce a second half-sin half-sinusoidal waveform. The RF output stage further includes a transformer having a primary winding and a secondary winding and a series inductor-capacitor resonant circuit, which are configured to generate a sinusoidal waveform.

14 Claims, 3 Drawing Sheets

U.S. PATENT DOCUMENTS

| | | |
|---|---|---|
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |

| Patent | Type | Date | Inventor |
|---|---|---|---|
| 4,767,999 | A * | 8/1988 | VerPlanck .................. 331/166 |
| 4,788,634 | A | 11/1988 | Schlecht et al. |
| 4,805,621 | A | 2/1989 | Heinze et al. |
| 4,818,954 | A | 4/1989 | Flachenecker et al. |
| 4,827,911 | A | 5/1989 | Broadwin et al. |
| 4,827,927 | A | 5/1989 | Newton |
| 4,832,024 | A | 5/1989 | Boussignac et al. |
| 4,848,335 | A | 7/1989 | Manes |
| 4,848,355 | A | 7/1989 | Nakamura et al. |
| 4,860,745 | A | 8/1989 | Farin et al. |
| 4,862,889 | A | 9/1989 | Feucht |
| 4,880,719 | A | 11/1989 | Murofushi et al. |
| 4,887,199 | A | 12/1989 | Whittle |
| 4,890,610 | A | 1/1990 | Kirwan et al. |
| 4,903,696 | A | 2/1990 | Stasz et al. |
| 4,907,589 | A | 3/1990 | Cosman |
| 4,922,210 | A | 5/1990 | Flachenecker et al. |
| 4,931,047 | A | 6/1990 | Broadwin et al. |
| 4,931,717 | A | 6/1990 | Gray et al. |
| 4,938,761 | A | 7/1990 | Ensslin |
| 4,942,313 | A | 7/1990 | Kinzel |
| 4,959,606 | A | 9/1990 | Forge |
| 4,961,047 | A | 10/1990 | Carder |
| 4,961,435 | A | 10/1990 | Kitagawa et al. |
| 4,966,597 | A | 10/1990 | Cosman |
| RE33,420 | E | 11/1990 | Sussman |
| 4,969,885 | A | 11/1990 | Farin |
| 4,992,719 | A | 2/1991 | Harvey |
| 4,993,430 | A | 2/1991 | Shimoyama et al. |
| 4,995,877 | A | 2/1991 | Ams et al. |
| 5,015,227 | A | 5/1991 | Broadwin et al. |
| 5,019,176 | A | 5/1991 | Brandhorst, Jr. |
| 5,024,668 | A | 6/1991 | Peters et al. |
| 5,029,588 | A | 7/1991 | Yock et al. |
| 5,087,257 | A | 2/1992 | Farin |
| 5,099,840 | A | 3/1992 | Goble et al. |
| 5,103,804 | A | 4/1992 | Abele et al. |
| 5,108,389 | A | 4/1992 | Cosmescu |
| 5,108,391 | A | 4/1992 | Flachenecker |
| 5,122,137 | A | 6/1992 | Lennox |
| 5,133,711 | A | 7/1992 | Hagen |
| 5,151,102 | A | 9/1992 | Kamiyama et al. |
| 5,152,762 | A | 10/1992 | McElhenney |
| 5,157,603 | A | 10/1992 | Scheller et al. |
| 5,160,334 | A | 11/1992 | Billings et al. |
| 5,162,217 | A | 11/1992 | Hartman |
| 5,167,658 | A | 12/1992 | Ensslin |
| 5,190,517 | A | 3/1993 | Zieve et al. |
| 5,196,008 | A | 3/1993 | Kuenecke |
| 5,196,009 | A | 3/1993 | Kirwan, Jr. |
| 5,201,900 | A | 4/1993 | Nardella |
| 5,207,691 | A | 5/1993 | Nardella |
| 5,230,623 | A | 7/1993 | Guthrie et al. |
| 5,233,515 | A | 8/1993 | Cosman |
| 5,249,121 | A | 9/1993 | Baum et al. |
| 5,254,117 | A | 10/1993 | Rigby et al. |
| RE34,432 | E | 11/1993 | Bertrand |
| 5,267,994 | A | 12/1993 | Gentelia et al. |
| 5,267,997 | A | 12/1993 | Farin |
| 5,281,213 | A | 1/1994 | Milder et al. |
| 5,300,068 | A | 4/1994 | Rosar et al. |
| 5,300,070 | A | 4/1994 | Gentelia |
| 5,318,563 | A | 6/1994 | Malis et al. |
| 5,323,778 | A | 6/1994 | Kandarpa et al. |
| 5,324,283 | A | 6/1994 | Heckele |
| 5,330,518 | A | 7/1994 | Neilson et al. |
| 5,334,183 | A | 8/1994 | Wuchinich |
| 5,334,193 | A | 8/1994 | Nardella |
| 5,341,807 | A | 8/1994 | Nardella |
| 5,342,356 | A | 8/1994 | Ellman |
| 5,342,357 | A | 8/1994 | Nardella |
| 5,342,409 | A | 8/1994 | Mullett |
| 5,348,554 | A | 9/1994 | Imran et al. |
| 5,370,645 | A | 12/1994 | Klicek et al. |
| 5,370,672 | A | 12/1994 | Fowler et al. |
| 5,370,675 | A | 12/1994 | Edwards et al. |
| 5,372,596 | A | 12/1994 | Klicek et al. |
| 5,383,874 | A | 1/1995 | Jackson |
| 5,383,876 | A | 1/1995 | Nardella |
| 5,383,917 | A | 1/1995 | Desai et al. |
| 5,385,148 | A | 1/1995 | Lesh et al. |
| 5,396,062 | A | 3/1995 | Eisentraut et al. |
| 5,400,267 | A | 3/1995 | Denen et al. |
| 5,403,311 | A | 4/1995 | Abele et al. |
| 5,403,312 | A | 4/1995 | Yates et al. |
| 5,409,000 | A | 4/1995 | Imran |
| 5,409,006 | A | 4/1995 | Buchholtz et al. |
| 5,409,485 | A | 4/1995 | Suda |
| 5,413,573 | A | 5/1995 | Koivukangas |
| 5,414,238 | A | 5/1995 | Steigerwald et al. |
| 5,417,719 | A | 5/1995 | Hull et al. |
| 5,422,567 | A | 6/1995 | Matsunaga |
| 5,423,808 | A | 6/1995 | Edwards et al. |
| 5,423,809 | A | 6/1995 | Klicek |
| 5,423,810 | A | 6/1995 | Goble et al. |
| 5,425,704 | A | 6/1995 | Sakurai et al. |
| 5,430,434 | A | 7/1995 | Lederer et al. |
| 5,432,459 | A | 7/1995 | Thompson |
| 5,433,739 | A | 7/1995 | Sluijter et al. |
| 5,434,398 | A | 7/1995 | Goldberg |
| 5,436,566 | A | 7/1995 | Thompson |
| 5,438,302 | A | 8/1995 | Goble |
| 5,443,463 | A | 8/1995 | Stern et al. |
| 5,445,635 | A | 8/1995 | Denen |
| 5,451,224 | A | 9/1995 | Goble et al. |
| 5,458,597 | A | 10/1995 | Edwards et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,478,303 | A | 12/1995 | Foley-Nolan et al. |
| 5,480,399 | A | 1/1996 | Hebborn |
| 5,483,952 | A | 1/1996 | Aranyi |
| 5,490,850 | A | 2/1996 | Ellman et al. |
| 5,496,312 | A | 3/1996 | Klicek |
| 5,496,313 | A | 3/1996 | Gentelia et al. |
| 5,500,012 | A | 3/1996 | Brucker et al. |
| 5,500,616 | A | 3/1996 | Ochi |
| 5,514,129 | A | 5/1996 | Smith |
| 5,520,684 | A | 5/1996 | Imran |
| 5,531,774 | A | 7/1996 | Schulman et al. |
| 5,534,018 | A | 7/1996 | Wahlstrand et al. |
| 5,536,267 | A | 7/1996 | Edwards et al. |
| 5,540,681 | A | 7/1996 | Strul et al. |
| 5,540,683 | A | 7/1996 | Ichikawa |
| 5,540,684 | A | 7/1996 | Hassler, Jr. |
| 5,540,724 | A | 7/1996 | Cox |
| 5,556,396 | A | 9/1996 | Cohen et al. |
| 5,558,671 | A | 9/1996 | Yates |
| 5,569,242 | A | 10/1996 | Lax et al. |
| 5,571,147 | A | 11/1996 | Sluijter et al. |
| 5,573,533 | A | 11/1996 | Strul |
| 5,584,830 | A | 12/1996 | Ladd et al. |
| 5,588,432 | A | 12/1996 | Crowley |
| 5,594,636 | A | 1/1997 | Schauder |
| 5,596,466 | A | 1/1997 | Ochi |
| 5,599,344 | A | 2/1997 | Paterson |
| 5,599,345 | A | 2/1997 | Edwards et al. |
| 5,599,348 | A | 2/1997 | Gentelia et al. |
| 5,605,150 | A | 2/1997 | Radons et al. |
| 5,613,966 | A | 3/1997 | Makower et al. |
| 5,613,996 | A | 3/1997 | Lindsay |
| 5,625,370 | A | 4/1997 | D'Hont |
| 5,626,575 | A | 5/1997 | Crenner |
| 5,628,745 | A | 5/1997 | Bek |
| 5,643,330 | A | 7/1997 | Holsheimer et al. |
| 5,647,869 | A | 7/1997 | Goble et al. |

| Patent | Date | Inventor |
|---|---|---|
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,674,217 A | 10/1997 | Wahlstrom et al. |
| 5,685,840 A | 11/1997 | Schechter et al. |
| 5,688,267 A | 11/1997 | Panescu et al. |
| 5,690,692 A | 11/1997 | Fleming |
| 5,693,042 A | 12/1997 | Boiarski et al. |
| 5,694,304 A | 12/1997 | Telefus et al. |
| 5,695,494 A | 12/1997 | Becker |
| 5,696,351 A | 12/1997 | Benn et al. |
| 5,696,441 A | 12/1997 | Mak et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,749,869 A | 5/1998 | Lindenmeier et al. |
| 5,749,871 A | 5/1998 | Hood et al. |
| 5,755,715 A | 5/1998 | Stern |
| 5,766,165 A | 6/1998 | Gentelia et al. |
| 5,769,847 A | 6/1998 | Panescu |
| 5,772,659 A | 6/1998 | Becker et al. |
| 5,792,138 A | 8/1998 | Shipp |
| 5,797,802 A | 8/1998 | Nowak |
| 5,797,902 A | 8/1998 | Netherly |
| 5,814,092 A | 9/1998 | King |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,846,236 A | 12/1998 | Lindenmeier et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,897,552 A | 4/1999 | Edwards et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,961,344 A | 10/1999 | Rosales et al. |
| 5,971,980 A | 10/1999 | Sherman |
| 5,976,128 A | 11/1999 | Schilling et al. |
| 5,983,141 A | 11/1999 | Sluijter et al. |
| 6,010,499 A | 1/2000 | Cobb |
| 6,014,581 A | 1/2000 | Whayne et al. |
| 6,033,399 A | 3/2000 | Gines |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,063,075 A | 5/2000 | Mihori |
| 6,063,078 A | 5/2000 | Wittkampf |
| 6,068,627 A | 5/2000 | Orszulak et al. |
| 6,074,386 A | 6/2000 | Goble et al. |
| 6,074,388 A | 6/2000 | Tockweiler et al. |
| 6,080,149 A | 6/2000 | Huang et al. |
| 6,093,186 A | 7/2000 | Goble |
| 6,102,497 A | 8/2000 | Ehr et al. |
| RE36,871 E | 9/2000 | Epstein |
| 6,113,591 A | 9/2000 | Whayne et al. |
| 6,113,596 A | 9/2000 | Hooven |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,217 A | 12/2000 | Kannenberg et al. |
| 6,171,304 B1 | 1/2001 | Netherly et al. |
| 6,188,211 B1 | 2/2001 | Rincon-Mora et al. |
| 6,203,541 B1 | 3/2001 | Keppel |
| 6,210,403 B1 | 4/2001 | Klicek |
| 6,222,356 B1 | 4/2001 | Taghizadeh-Kaschani |
| 6,228,080 B1 | 5/2001 | Gines |
| 6,228,081 B1 | 5/2001 | Goble |
| 6,231,569 B1 | 5/2001 | Bek |
| 6,235,020 B1 | 5/2001 | Cheng et al. |
| 6,238,387 B1 | 5/2001 | Miller, III |
| 6,238,388 B1 | 5/2001 | Ellman |
| 6,241,725 B1 | 6/2001 | Cosman |
| 6,245,065 B1 | 6/2001 | Panescu |
| 6,246,912 B1 | 6/2001 | Sluijter et al. |
| 6,251,106 B1 | 6/2001 | Becker et al. |
| 6,258,085 B1 | 7/2001 | Eggleston |
| 6,261,285 B1 | 7/2001 | Novak |
| 6,261,286 B1 | 7/2001 | Goble et al. |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,743 B1 | 6/2002 | Orszulak et al. |
| 6,416,509 B1 | 7/2002 | Goble et al. |
| 6,436,096 B1 | 8/2002 | Hareyama |
| 6,451,015 B1 | 9/2002 | Rittman, III et al. |
| 6,458,121 B1 | 10/2002 | Rosenstock |
| 6,464,689 B1 | 10/2002 | Qin |
| 6,464,696 B1 | 10/2002 | Oyama |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside et al. |
| 6,517,538 B1 | 2/2003 | Jacob et al. |
| 6,524,308 B1 | 2/2003 | Muller et al. |
| 6,547,786 B1 | 4/2003 | Goble |
| 6,558,376 B2 | 5/2003 | Bishop |
| 6,560,470 B1 | 5/2003 | Pologe |
| 6,562,037 B2 | 5/2003 | Paton |
| 6,565,559 B2 | 5/2003 | Eggleston |
| 6,573,248 B2 | 6/2003 | Ramasamy et al. |
| 6,575,969 B1 | 6/2003 | Rittman, III et al. |
| 6,582,427 B1 | 6/2003 | Goble et al. |

| | | | | | | |
|---|---|---|---|---|---|---|
| 6,620,157 B1 | 9/2003 | Dabney et al. | | 7,255,694 B2 | 8/2007 | Keppel |
| 6,623,423 B2 | 9/2003 | Sakurai | | 7,282,048 B2 | 10/2007 | Goble et al. |
| 6,629,973 B1 | 10/2003 | Wardell et al. | | 7,300,435 B2 | 11/2007 | Wham et al. |
| 6,635,057 B2 | 10/2003 | Harano | | 7,303,557 B2 | 12/2007 | Wham et al. |
| 6,645,198 B1 | 11/2003 | Bommannan et al. | | 7,364,577 B2 | 4/2008 | Wham et al. |
| 6,648,883 B2 | 11/2003 | Francischelli | | 7,367,972 B2 | 5/2008 | Francischelli et al. |
| 6,652,514 B2 | 11/2003 | Ellman | | RE40,388 E | 6/2008 | Gines |
| 6,663,623 B1 | 12/2003 | Oyama et al. | | 7,396,336 B2 | 7/2008 | Orszulak et al. |
| 6,663,624 B2 | 12/2003 | Edwards | | 2001/0014804 A1 | 8/2001 | Goble et al. |
| 6,666,860 B1 | 12/2003 | Takahashi | | 2001/0029315 A1 | 10/2001 | Sakurai et al. |
| 6,679,875 B2 | 1/2004 | Honda | | 2001/0031962 A1 | 10/2001 | Eggleston |
| 6,682,527 B2 | 1/2004 | Strul | | 2002/0035363 A1 | 3/2002 | Edwards et al. |
| 6,685,700 B2 | 2/2004 | Behl | | 2002/0035364 A1 | 3/2002 | Schoenman et al. |
| 6,685,701 B2 | 2/2004 | Orszulak et al. | | 2002/0052599 A1 | 5/2002 | Goble |
| 6,685,703 B2 | 2/2004 | Pearson et al. | | 2002/0068932 A1 | 6/2002 | Edwards |
| 6,689,131 B2 | 2/2004 | McClurken | | 2002/0107517 A1 | 8/2002 | Witt et al. |
| 6,692,489 B1 | 2/2004 | Heim | | 2002/0111624 A1 | 8/2002 | Witt et al. |
| 6,693,782 B1 | 2/2004 | Lash | | 2002/0151889 A1 | 10/2002 | Swanson et al. |
| 6,712,813 B2 | 3/2004 | Ellman | | 2002/0193787 A1 | 12/2002 | Qin |
| 6,730,080 B2 | 5/2004 | Harano | | 2003/0004510 A1 | 1/2003 | Wham et al. |
| 6,733,495 B1 | 5/2004 | Bek | | 2003/0060818 A1 | 3/2003 | Kannenberg |
| 6,733,498 B2 | 5/2004 | Paton | | 2003/0078572 A1 | 4/2003 | Pearson et al. |
| 6,740,079 B1 | 5/2004 | Eggers | | 2003/0139741 A1 | 7/2003 | Goble et al. |
| 6,740,085 B2 | 5/2004 | Hareyama | | 2003/0153908 A1 | 8/2003 | Goble |
| 6,755,825 B2 | 6/2004 | Shoenman et al. | | 2003/0163123 A1 | 8/2003 | Goble |
| 6,758,846 B2 | 7/2004 | Goble et al. | | 2003/0163124 A1 | 8/2003 | Goble |
| 6,783,523 B2 | 8/2004 | Qin | | 2003/0171745 A1 | 9/2003 | Francischelli |
| 6,786,905 B2 | 9/2004 | Swanson et al. | | 2003/0181898 A1 | 9/2003 | Bowers |
| 6,790,206 B2 | 9/2004 | Panescu | | 2003/0199863 A1 | 10/2003 | Swanson |
| 6,796,981 B2 | 9/2004 | Wham | | 2003/0225401 A1 | 12/2003 | Eggers et al. |
| 6,824,539 B2 | 11/2004 | Novak | | 2004/0002745 A1 | 1/2004 | Flemming |
| 6,830,569 B2 | 12/2004 | Thompson | | 2004/0015159 A1 | 1/2004 | Slater et al. |
| 6,843,789 B2 | 1/2005 | Goble | | 2004/0015163 A1 | 1/2004 | Buysse et al. |
| 6,849,073 B2 | 2/2005 | Hoey | | 2004/0015216 A1 | 1/2004 | DeSisto |
| 6,855,141 B2 | 2/2005 | Lovewell | | 2004/0019347 A1 | 1/2004 | Sakurai |
| 6,855,142 B2 | 2/2005 | Harano | | 2004/0024395 A1 | 2/2004 | Ellman |
| 6,860,881 B2 | 3/2005 | Sturm | | 2004/0030328 A1 | 2/2004 | Eggers |
| 6,864,686 B2 | 3/2005 | Novak | | 2004/0030330 A1 | 2/2004 | Brassell et al. |
| 6,875,210 B2 | 4/2005 | Refior | | 2004/0044339 A1 | 3/2004 | Beller |
| 6,893,435 B2 | 5/2005 | Goble | | 2004/0049179 A1 | 3/2004 | Francischelli |
| 6,923,804 B2 | 8/2005 | Eggers et al. | | 2004/0054365 A1 | 3/2004 | Goble |
| 6,929,641 B2 | 8/2005 | Goble et al. | | 2004/0059323 A1 | 3/2004 | Sturm et al. |
| 6,939,346 B2 | 9/2005 | Kannenberg et al. | | 2004/0068304 A1 | 4/2004 | Paton |
| 6,939,347 B2 | 9/2005 | Thompson | | 2004/0082946 A1 | 4/2004 | Malis |
| 6,942,660 B2 | 9/2005 | Pantera et al. | | 2004/0095100 A1 | 5/2004 | Thompson |
| 6,948,503 B2 | 9/2005 | Refior et al. | | 2004/0097912 A1 | 5/2004 | Gonnering |
| 6,966,907 B2 | 11/2005 | Goble | | 2004/0097914 A1 | 5/2004 | Pantera |
| 6,989,010 B2 | 1/2006 | Francischelli et al. | | 2004/0097915 A1 | 5/2004 | Refior |
| 6,994,704 B2 | 2/2006 | Qin et al. | | 2004/0116919 A1 | 6/2004 | Heim |
| 6,994,707 B2 | 2/2006 | Ellman et al. | | 2004/0133189 A1 | 7/2004 | Sakurai |
| 7,001,381 B2 | 2/2006 | Harano et al. | | 2004/0138653 A1 | 7/2004 | Dabney et al. |
| 7,004,174 B2 | 2/2006 | Eggers et al. | | 2004/0138654 A1 | 7/2004 | Goble |
| 7,041,096 B2 | 5/2006 | Malis et al. | | 2004/0143263 A1 | 7/2004 | Schechter et al. |
| 7,044,948 B2 | 5/2006 | Keppel | | 2004/0147918 A1 | 7/2004 | Keppel |
| 7,044,949 B2 | 5/2006 | Orszulak et al. | | 2004/0167508 A1 | 8/2004 | Wham et al. |
| 7,060,063 B2 | 6/2006 | Marion et al. | | 2004/0172016 A1 | 9/2004 | Bek |
| 7,062,331 B2 | 6/2006 | Zarinetchi et al. | | 2004/0193148 A1 | 9/2004 | Wham et al. |
| 7,063,692 B2 | 6/2006 | Sakurai et al. | | 2004/0230189 A1 | 11/2004 | Keppel |
| 7,066,933 B2 | 6/2006 | Hagg | | 2004/0243120 A1 | 12/2004 | Orszulak et al. |
| 7,094,231 B1 * | 8/2006 | Ellman et al. ............. 606/37 | | 2004/0260279 A1 | 12/2004 | Goble |
| 7,122,031 B2 | 10/2006 | Edwards et al. | | 2005/0004564 A1 | 1/2005 | Wham |
| 7,131,860 B2 | 11/2006 | Sartor et al. | | 2005/0004569 A1 | 1/2005 | Witt et al. |
| 7,137,980 B2 | 11/2006 | Buysse et al. | | 2005/0021020 A1 | 1/2005 | Blaha et al. |
| 7,147,638 B2 | 12/2006 | Chapman et al. | | 2005/0021022 A1 | 1/2005 | Sturm et al. |
| 7,160,293 B2 | 1/2007 | Sturm et al. | | 2005/0101949 A1 | 5/2005 | Harano et al. |
| 7,172,591 B2 | 2/2007 | Harano et al. | | 2005/0101951 A1 | 5/2005 | Wham |
| 7,175,618 B2 | 2/2007 | Dabney et al. | | 2005/0113818 A1 | 5/2005 | Sartor |
| 7,175,621 B2 | 2/2007 | Heim et al. | | 2005/0113819 A1 | 5/2005 | Wham |
| 7,211,081 B2 | 5/2007 | Goble | | 2005/0149151 A1 * | 7/2005 | Orszulak et al. ............. 607/96 |
| 7,214,224 B2 | 5/2007 | Goble | | 2005/0182398 A1 | 8/2005 | Paterson |
| 7,220,260 B2 | 5/2007 | Fleming et al. | | 2005/0197659 A1 | 9/2005 | Bahney |
| 7,247,155 B2 | 7/2007 | Hoey et al. | | 2005/0203504 A1 | 9/2005 | Wham et al. |
| 7,250,746 B2 | 7/2007 | Oswald et al. | | 2006/0025760 A1 | 2/2006 | Podhajsky |

| | | | |
|---|---|---|---|
| 2006/0079871 A1 | 4/2006 | Plaven et al. | |
| 2006/0161148 A1* | 7/2006 | Behnke ........................ 606/34 | |
| 2006/0178664 A1 | 8/2006 | Keppel | |
| 2006/0224152 A1 | 10/2006 | Behnke et al. | |
| 2006/0281360 A1 | 12/2006 | Sartor et al. | |
| 2007/0038209 A1 | 2/2007 | Buysse et al. | |
| 2007/0093800 A1 | 4/2007 | Wham et al. | |
| 2007/0093801 A1 | 4/2007 | Behnke | |
| 2007/0135812 A1 | 6/2007 | Sartor | |
| 2007/0173802 A1 | 7/2007 | Keppel | |
| 2007/0173803 A1 | 7/2007 | Wham et al. | |
| 2007/0173804 A1 | 7/2007 | Wham et al. | |
| 2007/0173805 A1 | 7/2007 | Weinberg et al. | |
| 2007/0173806 A1 | 7/2007 | Orszulak et al. | |
| 2007/0173810 A1 | 7/2007 | Orszulak | |
| 2007/0173813 A1 | 7/2007 | Odom | |
| 2007/0208339 A1 | 9/2007 | Arts et al. | |
| 2007/0225698 A1 | 9/2007 | Orszulak et al. | |
| 2007/0250052 A1 | 10/2007 | Wham | |
| 2007/0265612 A1 | 11/2007 | Behnke et al. | |
| 2007/0282320 A1 | 12/2007 | Buysse et al. | |
| 2008/0015564 A1 | 1/2008 | Wham et al. | |
| 2008/0039831 A1 | 2/2008 | Odom et al. | |
| 2008/0039836 A1 | 2/2008 | Odom et al. | |
| 2008/0082094 A1 | 4/2008 | McPherson et al. | |
| 2008/0125767 A1 | 5/2008 | Blaha | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1645235 | 4/2006 |
| EP | 0880220 B1 | 6/2006 |
| EP | 1707143 | 10/2006 |
| EP | 1810628 | 7/2007 |
| EP | 1810630 | 7/2007 |
| EP | 1810633 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 1290304 * | 9/1972 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060365 | 7/2005 |
| WO | WO2005/060849 | 7/2005 |

OTHER PUBLICATIONS

International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . ." Journal of Applied Sciences-Yingyong Kexue Xuebao, Shanghai CN, vol. 23 No. 2; (Mar. 2005); 160-164.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.

International Search Report EP07004355.9 dated May 21, 2007.

Muller et al., "Extended Left Hemicolectomy Using the LigaSure Vessel Sealing System" Innovations That Work; Sep. 1999.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al. "Studies on Coagulation and the Development of an Automatic Computerized Bipolar Coagulator" J.Neurosurg, vol. 75, Jul. 1991, pp. 148-151.

Chicharo et al. "A Sliding Goertzel Algorith" Aug. 1996, pp. 283-297 Signal Processing, Elsevier Science Publishers B.V. Amsterdam, NL vol. 52 No. 3.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedance" Am. J. MI, Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure "The O.R. Pro 300" 1 p. Sep. 1998.

Ogden Goertzel Alternative to the Fourier Transform: Jun. 1993 pp. 485-487 Electronics World: Reed Business Publishing, Sutton, Surrey, BG vol. 99, No. 9. 1687.

Sugita et al., "Bipolar Coagulator with Automatic Thermocontrol" J. Neurosurg., vol. 41, Dec. 1944, pp. 777-779.

Valleylab Brochure "Valleylab Electroshield Monitoring System" 2 pp. Nov. 1995.

Vallfors et al., "Automatically Controlled Bipolar Electrosoagulation-'COA-COMP'" Neurosurgical Review 7:2-3 (1984) pp. 187-190.

Wald et al., "Accidental Burns", JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp. Jan. 1989.

International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 07008207.8 dated Sep. 5, 2007.
International Search Report EP 07010673.7 dated Sep. 24, 2007.

* cited by examiner

US 7,513,896 B2

DUAL SYNCHRO-RESONANT ELECTROSURGICAL APPARATUS WITH BI-DIRECTIONAL MAGNETIC COUPLING

BACKGROUND

1. Field

The present disclosure relates generally to electrosurgical system, and more specifically, to an electrosurgical generator for delivering high power radiofrequency (RF) energy using multiple resonant inductor-capacitor (LC) networks and a switching module for adjusting the energy to make it suitable for a variety of electrosurgical procedures.

2. Description of the Related Art

Electrosurgery involves application of high radio frequency (RF) electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of a surgical instrument held by the surgeon and applied to the tissue to be treated. A patient return electrode is placed remotely from the active electrode to carry the current back to the generator.

In bipolar electrosurgery, a hand-held instrument typically carries two electrodes, e.g., electrosurgical forceps. One of the electrodes of the hand-held instrument functions as the active electrode and the other as the return electrode. The return electrode is placed in close proximity to the active (i.e., current supplying) electrode such that an electrical circuit is formed between the two electrodes. In this manner, the applied electrical current is limited to the body tissue positioned between the two electrodes.

In electrosurgery, radio frequency (RF) power is the preferred type of energy. However, RF energy must be generated having sufficient frequency, so that the RF energy may be used to cut, coagulate, etc. tissue by sustaining tissue thermal heating for prolonged periods of time. Current state of the art electrosurgical generators do not provide sufficiently powerful RF energy for prescribed periods of time. In addition, for each type of an electrosurgical procedure (e.g., monopolar, bipolar, vessel sealing) a different generator is used.

Therefore, there is a need for an electrosurgical generator which can develop high RF power with high efficiency and can be used to provide RF energy suitable for performing various types of electrosurgical procedures.

SUMMARY

The present disclosure provides for an electrosurgical generator which includes an RF output stage connected to a DC power supply. The RF output stage includes two connections which receive DC energy and are connected to a transformer. Each of the two connections includes a switching component that is cycled between on and off positions at the same frequency but in a 180 degree out-of-phase relationship and a parallel inductor-capacitor resonant circuit. The two connections also include a series inductor-capacitor resonant circuit oriented at a primary winding of the transformer. The first connection produces a first positive half-sinusoidal waveform and the second connection also produces a second positive half-sinusoidal waveform, which is phase-delayed 180 degrees with respect to the first positive half-sinusoidal waveform. The waveforms combine at the transformer to form a sine waveform suitable for electrosurgical procedures involving RF energy. The RF output stage also includes a switching module having two capacitors with each oriented in parallel with the capacitors of the parallel inductor-capacitor circuits. The switching module is controlled by a selection module which closes and opens three switches of the switching module to include the capacitors into the circuit thereby modifying the resulting sinusoidal wave.

The present disclosure also relates to an electrosurgical generator which includes a selection module configured to transmit control signals for adjusting the electrosurgical generator to produce sinusoidal waveforms suitable for the at least one electrosurgical mode and an RF output stage for generating sinusoidal waveforms for at least one electrosurgical mode. The RF output stage is connected to a DC power supply including first and second connections, the first connection includes a first switching component and a first parallel inductor-capacitor resonant circuit and a second connection includes a second switching components and a second parallel inductor-capacitor resonant circuit. The first and second switching components are configured to open and close at a predetermined frequency based on a phase-correlated dual drive signal emitted by a driver and are in a 180 degree out-of-phase relationship.

The first parallel inductor-capacitor resonant circuit is configured to produce a first positive half-sinusoidal waveform and the second parallel inductor-capacitor resonant circuit is configured to produce a second positive half-sinusoidal waveform, which is phase-delayed 180 degrees with respect to the first positive half-sinusoidal waveform. The RF output stage further includes a transformer having a primary winding and a secondary winding, which is a patient connective side, and a series inductor-capacitor resonant circuit. The series inductor-capacitor resonant circuit and the transformer are configured to generate a sinusoidal waveform. The RF output stage further includes a switching module which, in response to the control signals, adjusts the first and second half-sinusoidal waveforms thereby producing the sinusoidal waveforms suitable for the at least one electrosurgical mode. The first and second waveforms generate in-sync ripple components at the primary winding, which generate opposing magnetic fields thereby preventing transfer of parasitic RF harmonic ring energy to the secondary winding.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

The present disclosure includes an RF electrosurgical apparatus having a dual synchronous-resonant, magnetically coupled architecture which generates multi-mode and multi-frequency, monopolar, bipolar, and sealing type RF energy. RF energy is developed using a phase correlated dual drive network having a single or integer multiple number of drive pulses applies to switching devices which generate the dual synchronous-resonant RF energy, coupled in the magnetic field of a patient connective isolating transformer. Magnetically coupled RF energy is used to both generate the applied RF, used in clinical applications, and simultaneously cancel the unwanted parasitic RF harmonics during RF off periods. The RF harmonic unwanted energy is canceled when low duty cycle RF burst energy is repeatedly applied to the tissue site with a repetition rate frequency which is lower than the RF burst frequency. This architecture provides dynamic switching of high crest factor RF burst energy or low crest factor continuous sinusoidal RF delivered to the tissue for clinical efficacy to either individually coagulate blood vessels, seal vessels and cut tissue or simultaneously cut and coagulate tissue and vessels with hemostasis.

The generator according to the present disclosure can perform monopolar and bipolar electrosurgical procedures, including vessel sealing procedures. The generator includes a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
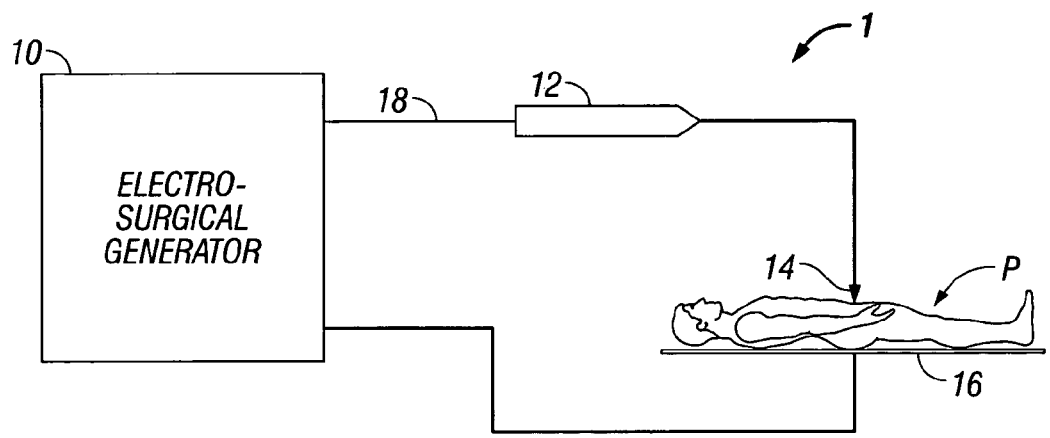
FIGS. 1A-1B are schematic block diagrams of an electrosurgical system according to the present disclosure.

FIG. 1A is a schematic illustration of an electrosurgical system 1 configured for a monopolar procedure. The system 1 includes an active electrode 14 and a return electrode 16 for treating tissue of a patient P. Electrosurgical RF energy is supplied to the active electrode 14 by a generator 10 via a cable 18 allowing the active electrode 14 to ablate, cut or coagulate the tissue. The return electrode 16 is placed at the patient P to return the energy from the patient P to the generator 10 via a cable 19.

The generator 10 includes input controls (e.g., buttons, activators, switches, etc.) for controlling the generator 10. The controls allow the surgeon to adjust power of the RF energy, waveform, and other parameters to achieve the desired waveform suitable for a particular task (e.g., cutting, coagulating, etc.). Disposed between the generator 10 and the active electrode 14 on the cable 18 is a hand piece 12, which includes a plurality of input controls which may be redundant with certain input controls of the generator 10. Placing the input controls at the hand piece 12 allows for easier and faster modification of RF energy parameters during the surgical procedure without having the surgeon divert his attention to the generator 10. It is also envisioned that a footswitch may be connected to the generator to control energy delivery during monopolar procedures.

Figure 1B:
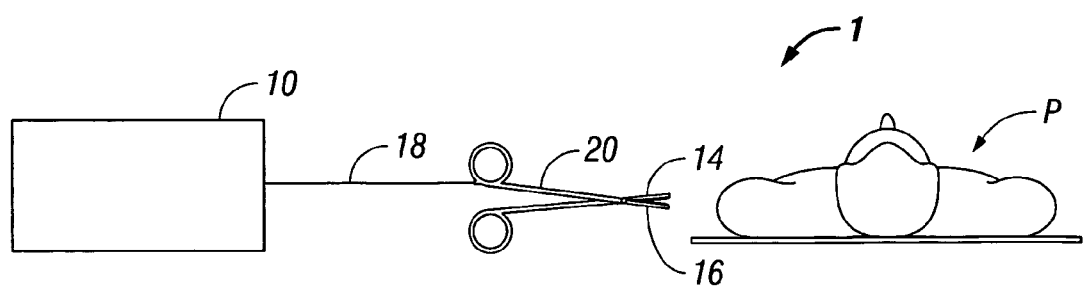

FIG. 1B is a schematic illustration of the electrosurgical system 1 configured for bipolar procedures. The active electrode 14 and the return electrode 16 are replaced by an electrosurgical forceps 20 which are connected to the generator 10 through the cable 18. More specifically, the electrosurgical forceps 20 include an active electrode 14 and a return electrode 16 disposed within jaws. The active electrode of the forceps 20 receives power from the cable 18 and the return electrode returns power via the cable 18.

Figure 2:
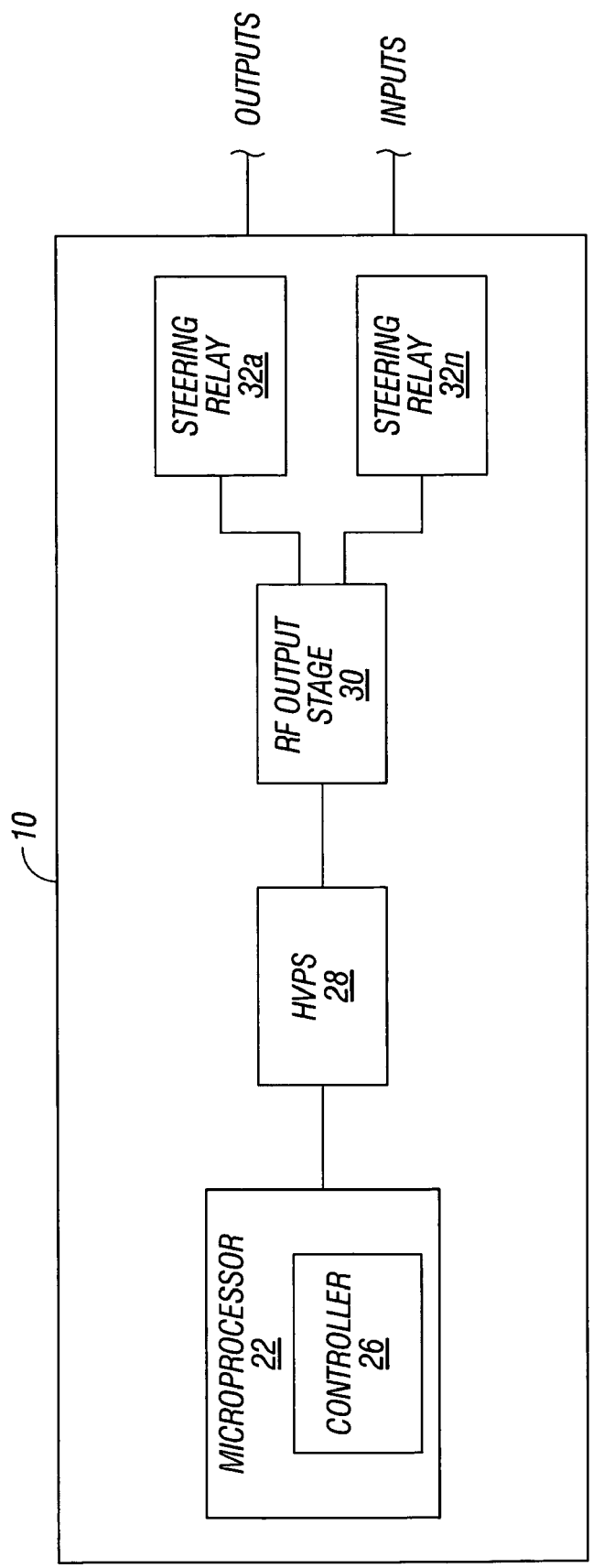
FIG. 2 is a schematic block diagram of a generator according to the present disclosure.

FIG. 2 shows a schematic block diagram of the generator 10 having a microprocessor 22, a high voltage DC power supply (HVPS) 28, and an RF output stage 30. The microprocessor 22 includes a controller 26 and an output port which is electrically connected to the HVPS 28 configured to supply DC voltage, from about 0 V to about 150 V, to the RF output stage 30. The microprocessor 22 receives input signals from the generator 10, the hand piece 12, or the footswitch and the controller 26, in turn, adjusts power outputted by the generator 10, more specifically the HVPS 28, and/or performs other control functions thereon.

The RF output stage 30 converts DC power into RF energy and delivers the RF energy, at about 470 KHz, to the active electrode 14, the forceps 20, or other electrosurgical devices connected to the generator 10. In addition, the RF output stage 30 also receives RF energy from the return electrode 16. More specifically, the RF output stage 30 is connected to one or more steering relays 32a-n. The steering relays 32a-n route RF energy from the RF output stage 30 to the multiple outputs of the generator 10, which may have a bipolar output configured for connection to the forceps 20, a monopolar output configured for connection to the active electrode 14, a footswitch output, etc. It is also envisioned that that the generator 10 may have multiple outputs of each type of output, e.g., the generator 10 can have two monopolar outputs and two bipolar outputs. This is particularly useful in electrosurgical procedures where multiple instruments are required (e.g., a smaller and a larger electrosurgical forceps configured for grasping tissue of various thicknesses). Only one output can be active at any one time, therefore, the steering relays 32a-n also provides isolation between the multiple outputs and their respective circuits.

Figure 3:
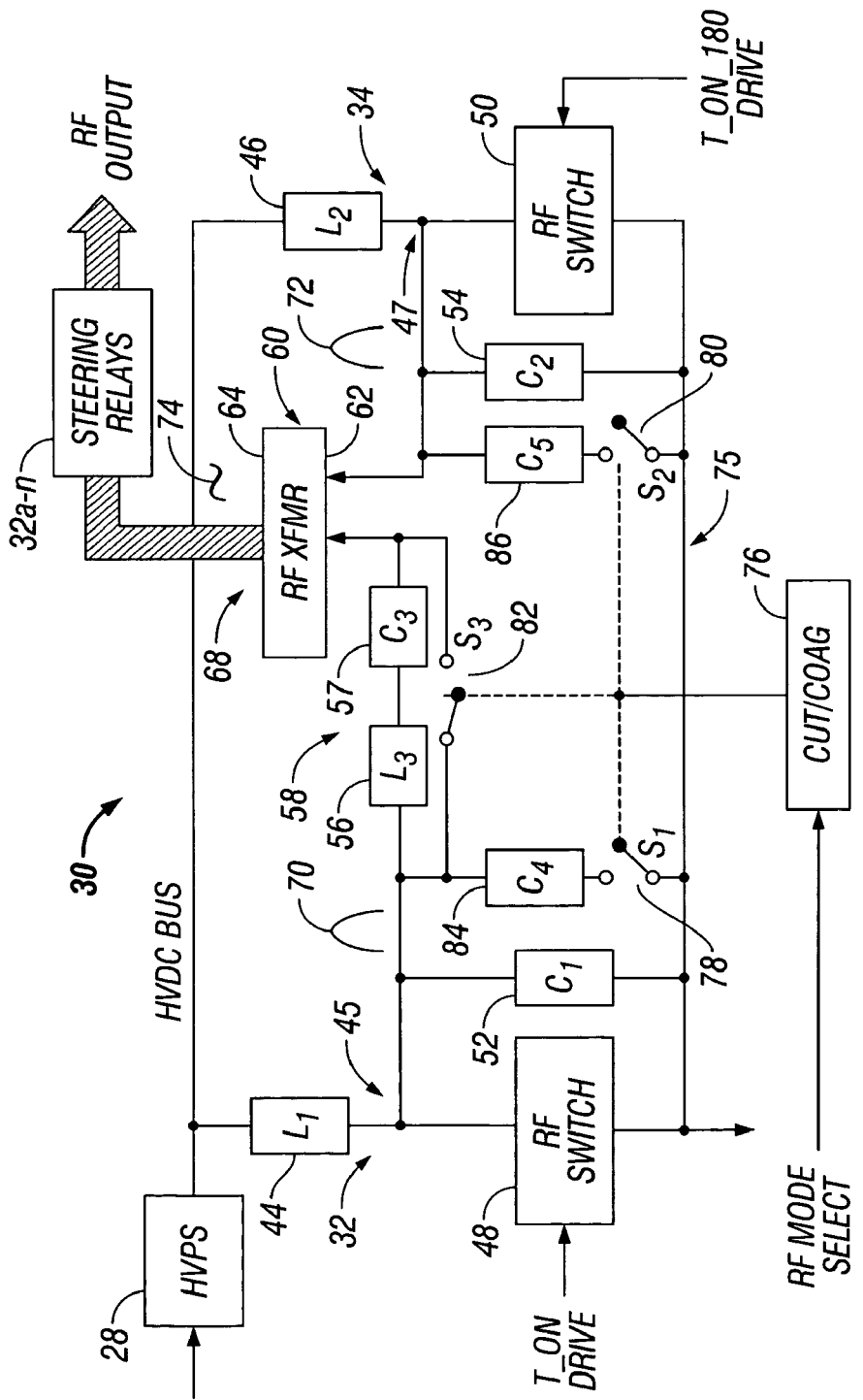
FIG. 3 is a circuit diagram of a radio frequency (RF) output stage according to the present disclosure.

The RF output stage 30 is shown in more detail in FIG. 3. The RF output stage 30 receives DC voltage from the HVPS 28 wherein first and second connections 32, 34 of a first winding 62 of a transformer 60 create two half-sinusoidal waveforms 180° out-of-phase which then combine at a secondary winding 64 of the transformer 60 to form a pure (e.g., full) sinusoidal waveform.

The power of the HVPS 28 can be varied to modify RF magnitude (e.g., amplitude) thereby adjusting the power of the RF energy delivered to the tissue. This allows for accurate regulation of the power of delivered RF energy.

The first and second connections 32, 34 include switching components 48, 50 and parallel inductor-capacitor resonant circuits 45, 47 (parallel LC circuits 45, 47), respectively. The switching components 48, 50 can be, for example, transistors, such as metal-oxide semiconductor field-effect transistors (MOSFET), insulated gate bipolar transistors (IGBT), relays, and the like. The switching components 48, 50 are turned on and off at a predetermined frequency which is also the operating frequency of the generator 10, thereby closing and opening the first and second connections 32, 34 respectively. The frequency at which the switching components 48, 50 are turned on and off is controlled by a driver (not shown). The driver emits a phase-correlated (e.g., the switching components 48, 50 have a phase relationship) dual drive signal, (T_ON DRIVE and T_ON_180 DRIVE) more simply put, the driver signal cycles the switching components 48, 50 between on and off positions at the same frequency but out of sync, to create two half-sinusoidal waveforms 180° out-of-phase. Therefore, adjusting the phase-correlated dual drive signal provides a means for varying operating RF frequency. Pulsing of the phase-correlated dual drive signal also provides means for RF duty cycle control.

Each of the first and second connections 32, 34 includes the parallel LC circuits 45, 47, respectively, which convert DC electrical energy into RF energy (e.g., AC energy having a high frequency from about 300 kHz to about 1000 kHz). The parallel LC circuits 45, 47 include inductors 44, 46 connected in parallel with first capacitors 52, 54 respectively. When the switching components 48, 50 are closed, DC power is supplied to the inductors 44, 46 which thereafter discharge through the first capacitors 52, 54, respectively, when the switching components 48, 50 are open. This process converts the constant pulse of DC energy into half-sinusoidal waveforms 70, 72 by the first and second connections 32, 34 respectively. Since the switching components 48, 50 turn on and off at the same frequency but 180° out-of-phase, the resulting half-sinusoidal waveforms 70, 72 are also 180° out-of-phase.

The first and second connections 32, 34 also include a series inductor-capacitor (LC) resonant circuit 58 which includes an inductor 56 and a capacitor 57 coupled to the second connection 34 of the primary winding 62. The series LC circuit 58 and the parallel LC circuits 45, 47 each have a resonant operating frequency which is mode dependant. The series resonant LC circuit 58 may be within 50 kHz of the operating frequency, which may be about 424 kHz. The parallel resonant LC circuits 45, 47 may be within 20 kHz of the operating frequency, which may be about 490 kHz. The resonant frequency is based on the inductance and capacitance values of the series LC circuit 58 and the parallel LC circuits 45, 47. The inductance of the inductors 44, 46, 56 and capacitance of the capacitors 52, 54, 57, 84, 86 should be selected to maximize the RF power developed for performing medical procedures. Inductors 44, 46 may be about 3.5 μhy each, with inductor 56 at 44 μhy. Capacitors 52, 54 may be both 0.025 μf and capacitors 84, 86 may be both 0.033 μf, with capacitor 57 having a value of 3.2 nf. The primary winding 62 inductance contributes to the series and parallel resonant LC tune and is optimized dependent on the delivered RF energy.

The inductor 56 and the capacitor 57 can be oriented in a plurality of ways. The alternate orientations have no effect on the functionality of the first and second connections 32, 34. In one embodiment, the inductor 56 and the capacitor 57 are coupled in series to the first connection 32, with the capacitor 57 coupled between the primary winding 62 and the inductor 56. It is also envisioned that the capacitor 57 is coupled to the second connection 34 and the inductor 56 is oriented to the first connection 32. In another embodiment, the capacitor 57 is coupled to the first connection 32 and the inductor 56 is coupled to the second connection 34. In a further embodiment, the inductor 56 and the capacitor 57 are coupled to the second connection 34, with the inductor 56 being oriented between the primary winding 62 and the capacitor 57.

As discussed above, the switching components 48, 50 are alternately switched on and off at the same frequency by the phase correlated dual drive signal (T_ON DRIVE and T_ON_180 DRIVE). This synchronizes the parallel LC circuits 45, 47 and the series LC circuit 58 and develops the half-sinusoidal waveforms 70, 72. The half-sinusoidal waveform 70 is magnetically coupled through the transformer 60 to develop a positive half-sine voltage to a patient-connective side 68 leading to the active electrode 14. The half-sinusoidal waveform 72 is coupled through the transformer 60 to develop a second positive half-sine voltage. The half-sinusoidal waveforms 70, 72 combine on the secondary winding (e.g., the patient-connective side 68) to generate a pure sine wave 74 because the half-sinusoidal waveforms 70, 72 are 180° out-of-phase.

The RF output stage 30 also includes a switching circuit 75 for switching between multiple modes of operation of the generator 10, such as cutting, blending, division, fulguration, ablation, vessel sealing and coagulation. It is envisioned that certain modes can be used in bipolar and monopolar procedures (e.g., cutting, blending, division, etc.) while others are best suited for uses during specific procedures (e.g., ablation via monopolar and vessel sealing via bipolar).

The switching circuit 75 includes switches 78, 80, 82 and a capacitor 84 which along with the switch 78 is parallel with the capacitor 52 and a capacitor 86 which along with the switch 80 is parallel with the capacitor 54. The capacitors 84, 86 modify the waveform generated at the first and second connections 32, 34 when the switches 78, 80, 82 are closed. The switches 78, 80, 82 can be FET switches or relays. The capacitors 84, 85 modify the timing of the half-sine waveforms 70, 72 at connections 32, 34 by changing the resonant tune.

The switches 78, 80, 82 are controlled by a mode selection module 76 which receives control signals (e.g., selecting a specific mode) from the inputs of the generator 10 or the hand piece 12. Depending on which mode is chosen, the mode selection module 76 closes and/or opens corresponding switches. The cut mode is chosen with switches 78 and 80 closed and switch 82 open. Coagulation modes (e.g., blend, division with hemostatis, and fulgurate) operate with all of the switches 78, 80, 82 being in close position. Other modes are envisioned where the switch 82 is closed and switches 78 and 80 are open to achieve a higher tune parallel resonant network.

The RF output stage 30 is capable of generating a variety of waveforms suitable for performing specific electrosurgical procedures. For example, in cutting mode, the RF output stage generates a 473 kHz continuous sine wave with a crest factor of 1.5 or less, the duty cycle is 100%. In blend mode, the RF output stage 30 generates bursts of 473 kHz sine wave reoccurring at a 26.2 kHz rate, with the duty cycle of the bursts being 50%. In the blend mode, the crest factor of one period of the sine wave is less than 1.5 and the crest factor of the 26.2 kHz burst will be between 2.3 and 2.7. The division mode which is defined as "division with hemostatis," includes bursts of 473 kHz sine wave reoccurring at a 28.3 kHz rate, with the duty cycle being 25%; the crest factor of each of the 28.3 kHz bursts will be 3.2 to 4.3 with impedance being from about 100 Ohms to about 2,000 Ohms. The fulgurate mode includes bursts of 473 kHz sine wave reoccurring at a 30.7 kHz rate having a duty cycle of the bursts be about 6.5%; the crest factor of each of the bursts is from about 5.5 to about 7.2 with impedance being also from about 100 Ohms to about 2,000 Ohms.

The present disclosure provides for an electrosurgical generator which includes coupled series and parallel resonant LC networks. The LC networks permit development of high RF power without sacrificing high efficiency. In addition, the generator according to the present disclosure provides increasing lesion creation capability, more specifically, the generator allows for creation of larger ablation volumes in tissue. This is due to reduced power loss attributable to the coupled LC resonant topology, which minimizes the need for additional heat removal associated with high power RF energy generation processes. The dual resonant topology, with combined series and parallel LC resonant circuits provides efficient energy transfer between reactive LC component which consume minimal power loss. The LC network generates less heat as a result of the reactive impedance compared to the real power loss associated with resistive elements.

The electrosurgical generator according to the present disclosure provides many advantages. For example, the generator has multiple RF based operating modes (e.g., monopolar, bipolar, sealing, etc.) which produce suitable type RF energy from either single or multiple RF sources. The generator also generates synchronous-resonant RF energy, which is coupled in the magnetic field of the patient connective isolation transformer. Magnetically coupled RF energy is used to both generate the applied RF, used in clinical applications, and simultaneously cancel the unwanted parasitic RF harmonics during RF off periods, when low duty cycle RF burst energy is repeatedly applied to the tissue site with a repetition rate frequency lower than the RF burst frequency. Magnetic coupling of the dual resonant RF also creates automatic damping of RF ring energy during off periods, without the need for damping components with low duty cycle coagulation waveforms applied to tissue loads.

In particular, the RF topology illustrated in FIG. 3 is uniquely configured such that the synchronously phased waveforms of 70, 72 generate in-sync ripple components, impressed upon the primary 62 winding of the transformer 60 at the completion of their respective half-sine waveforms. These ripple voltages generate an opposing magnetic field coupling in the primary winding 62 equivalent to the common mode rejection principle, such that the unwanted parasitic RF harmonics do not transfer to the secondary winding 68 of the patient connective transformer 60. As a result, the RF output stage 30 automatically cancels the parasitic Rf content during the RF off periods, independent of the variable low duty RF waveforms, for the RF modes such as blend, fulgurate, division with hemostatis, spray, etc.

The generator also allows for dynamic RF switching of high crest factor RF burst energy or low crest factor continuous sinusoidal RF delivered to the tissue. This allows for clinical efficacy to either individually coagulate or seal vessels and cut tissue or simultaneously cut and coagulate tissue and vessels with hemostasis. The generator also provides additional advantages: 1) the generator provides multiple RF operating frequencies from a single RF source by altering tuning of the RF; 2) the generator provides a phase correlated dual drive network, having singular and integer multiple number of drive pulses applied to switching device which generate the dual synchronous-resonant RF energy; 3) the generator provides RF operating modes are selected and processed on the ground referenced primary side of the patient connective isolation transformer thereby providing a fast RF response for clinical applications; 4) the generator does not allow energy storage or filter components to be present on the patient connective output; 5) there are no RF output surging or back emf effects result with rapid tissue desiccation and arcing due to the removal of output energy storage and filter components; 6) the generator provides controlled RF delivery in the presence of delivered arc energy; and 7) the generator provides high immunity to disruptive arc energy in vessel sealing mode due to the elimination of output energy storage and filter components.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical generator comprising:
   a selection module configured to transmit control signals which adjusts the electrosurgical generator to produce sinusoidal waveforms suitable for the at least one electrosurgical mode;
   an RF output stage which generates sinusoidal waveforms for at least one electrosurgical mode, the RF output stage connected to a DC power supply including first and second connections, the first connection including a first switching component and a first parallel inductor-capacitor resonant circuit and the second connection including a second switching components and a second parallel inductor-capacitor resonant circuit, the first and second switching components being configured to open and close at a predetermined frequency based on a phase-correlated dual drive signal emitted by a driver and are in a 180 degree out-of-phase relationship, the first parallel inductor-capacitor resonant circuit being configured to produce a first half-sinusoidal waveform and the second parallel inductor-capacitor resonant circuit being configured to produce a second half-sinusoidal waveform, the RF output stage including:
   a transformer having a primary winding and a secondary winding and a series inductor-capacitor resonant circuit, the series inductor-capacitor resonant circuit and the transformer configured to generate a sinusoidal waveform;
   a switching module which, in response to the control signals, adjusts the first and second half-sinusoidal waveforms thereby producing the sinusoidal waveforms suitable for the at least one electrosurgical mode.

2. An electrosurgical generator as in claim 1, wherein the first parallel inductor-capacitor resonant circuit is tuned to a first self-resonant frequency which is substantially equivalent to the predetermined frequency.

3. An electrosurgical generator as in claim 2, wherein the first parallel inductor-capacitor resonant circuit includes a first inductor having a first inductance value and a first capacitor having a first capacitance value, wherein the first inductance value and the first capacitance correspond to the first self-resonant frequency.

4. An electrosurgical generator as in claim 1, wherein the second parallel inductor-capacitor resonant circuit is tuned to a second self-resonant frequency which is substantially equivalent to the predetermined frequency.

5. An electrosurgical generator as in claim 4, wherein the second parallel inductor-capacitor resonant circuit includes a second inductor having a second inductance value and a second capacitor having a second capacitance value, wherein the second inductance value and the second capacitance correspond to the second self-resonant frequency.

6. An electrosurgical generator as in claim 1, wherein the first and second switching components are selected from the group consisting of transistors and relays.

7. An electrosurgical generator as in claim 1, wherein the first and second switching components are selected from the group consisting of metal-oxide semiconductor field-effect transistors and insulated gate bipolar transistors.

8. An electrosurgical generator as in claim 1, wherein the series inductor-capacitor resonant circuit is tuned to a third self-resonant frequency which is substantially equivalent to the predetermined frequency.

9. An electrosurgical generator as in claim 8, wherein the series inductor-capacitor resonant circuit includes a third inductor having a third inductance value and a third capacitor having a third capacitance value, wherein the third inductance value and the third capacitance correspond to the third self-resonant frequency.

10. An electrosurgical generator as in claim 1, wherein the switching module includes a fourth capacitor and a first switch in parallel with the first capacitor, a fifth capacitor and a second switch in parallel with the second capacitor, and a third switch in parallel with the series inductor-capacitor resonant circuit.

11. An electrosurgical generator as in claim 1, wherein the at least one electrosurgical mode is selected from the group consisting of cutting, blending, division with hemostasis, fulguration, ablation, vessel sealing and coagulation.

12. An electrosurgical generator as in claim 1, further including at least one output configured to interface with an electrosurgical instrument suitable for a specific electrosurgical procedure.

13. An electrosurgical generator as in claim 12, wherein the electrosurgical procedure is selected from the group consisting of bipolar, monopolar, vessel sealing and ablation.

14. An electrosurgical generator as in claim 1, wherein first and second half-sinusoidal waveforms generate in-sync ripple components at the primary winding thereby producing opposing magnetic fields which prevent transfer of parasitic RF harmonic ring energy to the secondary winding.

* * * * *